(12) United States Patent
Goffin et al.

(10) Patent No.: US 8,263,340 B2
(45) Date of Patent: Sep. 11, 2012

(54) CONSTITUTIVELY ACTIVE MUTANTS OF THE PROLACTIN RECEPTOR

(75) Inventors: Vincent Goffin, Orgerus (FR); Philippe Touraine, Paris (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 12/532,063

(22) PCT Filed: Mar. 20, 2007

(86) PCT No.: PCT/IB2007/001666
§ 371 (c)(1),
(2), (4) Date: Sep. 18, 2009

(87) PCT Pub. No.: WO2008/114077
PCT Pub. Date: Sep. 25, 2008

(65) Prior Publication Data
US 2010/0240033 A1    Sep. 23, 2010

(51) Int. Cl.
*C12Q 1/68*    (2006.01)
(52) U.S. Cl. .................................. 435/6.14; 435/6.1
(58) Field of Classification Search ............... None
See application file for complete search history.

(56) References Cited

U.S. PATENT DOCUMENTS
2002/0156023 A1    10/2002    Walling et al.

FOREIGN PATENT DOCUMENTS

| WO | WO 99/58142 | 11/1999 |
|----|-------------|---------|
| WO | WO-02-50098 A2 * | 6/2002 |
| WO | WO 03/057729 | 7/2003 |
| WO | WO 2005/058232 | 6/2005 |

OTHER PUBLICATIONS

Goffin, et al., "Development and Potential Clinical Uses of Human Prolactin Receptor Antagonists", Endocrine Reviews, 26:3, 2005, pp. 400-422.
Vaclavicek, et al. "Association of Prolactin and its Receptor Gene Regions with Familial Breast Cancer", The Journal of Clinical Endocrinology & Metabolism, 91:4, 2006, pp. 1513-1519.
Meng, et al. "Human Prolactin Receptor Variants in Breast Cancer: Low Ratio of Short Forms to the Long-Form Human Prolactin Receptor Associated with Mammary Carcinoma", Cancer Research, 64:16, 2004, pp. 5677-5682.
Gourdou, et al., "Expression by Transgenesis of a Constitutively Active Mutant Form of the Prolactin Receptor Induces Premature Abnormal Development of the Mouse Mammary Gland and Lactation Failure", Biology of Reproduction, 70:3, 2004, pp. 718-728.
Gourdou, et al., "Development of a Constitutively Active Mutant Form of the Prolactin Receptor, a Member of the Cytokine Receptor Family", Molecular Endocrinology, 10:1, 1996, pp. 45-56.
Goffin, et al., "Alanine-Scanning Mutagenesis of Human Prolactin: Importance of the 58-74 Region for Bioactivity", Molecular Endocrinology, 6:9, 1992, pp. 1381-1392.

* cited by examiner

*Primary Examiner* — James Martinell
(74) *Attorney, Agent, or Firm* — Morgan, Lewis & Bockius LLP

(57) ABSTRACT

The invention relates to constitutively active mutants of the prolactin receptor (PRLR), wherein an Ile residue at position 76 or at position 146 of the mature form of said receptor has been substituted by another amino acid residue. The invention also provides methods useful for the diagnosis, prognosis, or treatment of diseases involving the PRLR.

9 Claims, 12 Drawing Sheets

SEQUENCE LISTING

```
<160> NUMBER OF SEQ ID NOS: 5

<210> SEQ ID NO 1
<211> LENGTH: 598
<212> TYPE: PRT
<213> ORGANISM: Homo sapiens
<220> FEATURE:
<221> NAME/KEY: Variant
<222> LOCATION: (76)..(76)
<223> OTHER INFORMATION: Ile or Val
<220> FEATURE:
<221> NAME/KEY: Variant
<222> LOCATION: (146)..(146)
<223> OTHER INFORMATION: Ile or Val
```

<400> SEQUENCE: 1

```
Gln Leu Pro Pro Gly Lys Pro Glu Ile Phe Lys Cys Arg Ser Pro Asn
1               5                   10                  15

Lys Glu Thr Phe Thr Cys Trp Trp Arg Pro Gly Thr Asp Gly Gly Leu
            20                  25                  30

Pro Thr Asn Tyr Ser Leu Thr Tyr His Arg Glu Gly Glu Thr Leu Met
        35                  40                  45

His Glu Cys Pro Asp Tyr Ile Thr Gly Gly Pro Asn Ser Cys His Phe
    50                  55                  60

Gly Lys Gln Tyr Thr Ser Met Trp Arg Thr Tyr Xaa Met Met Val Asn
65                  70                  75                  80

Ala Thr Asn Gln Met Gly Ser Ser Phe Ser Asp Glu Leu Tyr Val Asp
                85                  90                  95

Val Thr Tyr Ile Val Gln Pro Asp Pro Pro Leu Glu Leu Ala Val Glu
            100                 105                 110

Val Lys Gln Pro Glu Asp Arg Lys Pro Tyr Leu Trp Ile Lys Trp Ser
        115                 120                 125

Pro Pro Thr Leu Ile Asp Leu Lys Thr Gly Trp Phe Thr Leu Leu Tyr
    130                 135                 140

Glu Xaa Arg Leu Lys Pro Glu Lys Ala Ala Glu Trp Glu Ile His Phe
145                 150                 155                 160

Ala Gly Gln Gln Thr Glu Phe Lys Ile Leu Ser Leu His Pro Gly Gln
                165                 170                 175

Lys Tyr Leu Val Gln Val Arg Cys Lys Pro Asp His Gly Tyr Trp Ser
            180                 185                 190

Ala Trp Ser Pro Ala Thr Phe Ile Gln Ile Pro Ser Asp Phe Thr Met
        195                 200                 205

Asn Asp Thr Thr Val Trp Ile Ser Val Ala Val Leu Ser Ala Val Ile
    210                 215                 220

Cys Leu Ile Ile Val Trp Ala Val Ala Leu Lys Gly Tyr Ser Met Val
225                 230                 235                 240

Thr Cys Ile Phe Pro Pro Val Pro Gly Pro Lys Ile Lys Gly Phe Asp
                245                 250                 255

Ala His Leu Leu Glu Lys Gly Lys Ser Glu Glu Leu Leu Ser Ala Leu
            260                 265                 270

Gly Cys Gln Asp Phe Pro Pro Thr Ser Asp Tyr Glu Asp Leu Leu Val
        275                 280                 285

Glu Tyr Leu Glu Val Asp Asp Ser Glu Asp Gln His Leu Met Ser Val
    290                 295                 300

His Ser Lys Glu His Pro Ser Gln Gly Met Lys Pro Thr Tyr Leu Asp
305                 310                 315                 320

Pro Asp Thr Asp Ser Gly Arg Gly Ser Cys Asp Ser Pro Ser Leu Leu
                325                 330                 335

Ser Glu Lys Cys Glu Glu Pro Gln Ala Asn Pro Ser Thr Phe Tyr Asp
            340                 345                 350

Pro Glu Val Ile Glu Lys Pro Glu Asn Pro Glu Thr Thr His Thr Trp
        355                 360                 365

Asp Pro Gln Cys Ile Ser Met Glu Gly Lys Ile Pro Tyr Phe His Ala
    370                 375                 380

Gly Gly Ser Lys Cys Ser Thr Trp Pro Leu Pro Gln Pro Ser Gln His
385                 390                 395                 400

Asn Pro Arg Ser Ser Tyr His Asn Ile Thr Asp Val Cys Glu Leu Ala
                405                 410                 415
```

```
Val Gly Pro Ala Gly Ala Pro Ala Thr Leu Leu Asn Glu Ala Gly Lys
            420                 425                 430

Asp Ala Leu Lys Ser Ser Gln Thr Ile Lys Ser Arg Glu Glu Gly Lys
    435                 440                 445

Ala Thr Gln Gln Arg Glu Val Glu Ser Phe His Ser Glu Thr Asp Gln
450                 455                 460

Asp Thr Pro Trp Leu Leu Pro Gln Glu Lys Thr Pro Phe Gly Ser Ala
465                 470                 475                 480

Lys Pro Leu Asp Tyr Val Glu Ile His Lys Val Asn Lys Asp Gly Ala
                485                 490                 495

Leu Ser Leu Leu Pro Lys Gln Arg Glu Asn Ser Gly Lys Pro Lys Lys
            500                 505                 510

Pro Gly Thr Pro Glu Asn Asn Lys Glu Tyr Ala Lys Val Ser Gly Val
        515                 520                 525

Met Asp Asn Asn Ile Leu Val Leu Val Pro Asp Pro His Ala Lys Asn
530                 535                 540

Val Ala Cys Phe Glu Glu Ser Ala Lys Glu Ala Pro Pro Ser Leu Glu
545                 550                 555                 560

Gln Asn Gln Ala Glu Lys Ala Leu Ala Asn Phe Thr Ala Thr Ser Ser
                565                 570                 575

Lys Cys Arg Leu Gln Leu Gly Gly Leu Asp Tyr Leu Asp Pro Ala Cys
            580                 585                 590

Phe Thr His Ser Phe His
        595

<210> SEQ ID NO 2
<211> LENGTH: 20
<212> TYPE: DNA
<213> ORGANISM: Artificial sequence
<220> FEATURE:
<223> OTHER INFORMATION: Synthetic PCR primer

<400> SEQUENCE: 2
ccagtggtat tgatctatga                                               20

<210> SEQ ID NO 3
<211> LENGTH: 20
<212> TYPE: DNA
<213> ORGANISM: Artificial sequence
<220> FEATURE:
<223> OTHER INFORMATION: Synthetic PCR primer

<400> SEQUENCE: 3
gtaagaaatt cctcacccac                                               20

<210> SEQ ID NO 4
<211> LENGTH: 20
<212> TYPE: DNA
<213> ORGANISM: Artificial sequence
<220> FEATURE:
<223> OTHER INFORMATION: Synthetic PCR primer

<400> SEQUENCE: 4
aaaggtgcaa gcaatgagtg                                               20
```

```
<210> SEQ ID NO 5
<211> LENGTH: 20
<212> TYPE: DNA
<213> ORGANISM: Artificial sequence
<220> FEATURE:
<223> OTHER INFORMATION: Synthetic PCR primer

<400> SEQUENCE: 5
ccaacacagt gacccagtaa                                               20
```

CONSTITUTIVELY ACTIVE MUTANTS OF THE PROLACTIN RECEPTOR

RELATED APPLICATIONS

The present application is a U.S. National Phase Application of International Application PCT/IB2007/001666, filed Mar. 20, 2007, which is herein incorporated by reference in its entirety.

SEQUENCE LISTING

A computer readable text file, entitled "045636-5117-US-SeqListing.txt," created on or about Apr. 8, 2010 with a file size of about 7 kb contains the sequence listing for this application and is hereby incorporated by reference in its entirety.

The invention relates to the identification of mutations resulting in a constitutive activation in the prolactin receptor.

Prolactin (PRL) is an anterior pituitary hormone involved in a wide spectrum of biological activities, among which are those related to lactation and reproduction. PRL actions on target tissues are mediated by a specific membrane-bound receptor, the prolactin receptor (PRLR), which belongs to the cytokine receptor superfamily (KELLY et al., Endocr. Rev., 12, 235-251, 1991). As most of the cytokines receptors, the PRLR activates the JAK/STAT pathway of signal transduction. Briefly, binding of PRL is assumed to induce PRLR dimerization and the consequent recruitment of one or more associated JAK tyrosine kinases (mainly JAK2), which causes trans-phosphorylation of both the JAK kinases and subsequent phosphorylation of the PRLR. The phosphorylated JAKs subsequently phosphorylate the STAT transcription factors (mainly STAT5) which dimerize and become able to translocate to the nucleus where they activate target genes.

In humans, it has been shown that PRL is also synthesized in many extra-pituitary sites, such as mammary epithelial cells or prostate. In addition, it was shown that the hormone exerts a proliferative action on these cells (expressing the PRLR) via an autocrine/paracrine loop, and it has been suggested that the growth-promoting activity exerted by PRL on some target tissues under normal conditions may be somehow involved in promoting tumor growth under pathological conditions.

In rodent model systems, it has been shown that PRL plays a key role in the development of mammary and prostate cancer and benign tumors. Although the role of PRL and PRLR in tumorigenesis in humans is not clear, there is increasing suspicion that they may be involved in the development of breast cancer. Attempts to identify potential mutations of the PRLR have been performed in patients with breast cancer (GLASOW et al., J Clin Endocrinol Metab, 86, 3826-3832, 2001), but they did not detect any polymorphisms in the coding sequence of the PRLR gene in 30 patients with mammary carcinomas. On the other hand, CANBAY et al., (Curr Med Res Opin, 20, 533-540, 2004) reported the detection, in two out of 38 patients with breast cancer, of a polymorphism in exon 6 of the PRLR gene, (A150C transversion resulting in a Leu→Ile substitution in the encoded protein). However, they found no correlation of this polymorphism with other pathological parameters of the tumour, and the biological relevance of this polymorphism as well as its eventual consequences on the properties of the PRL receptor remained unstudied.

In the case of benign (non cancerous) breast diseases, the involvement of PRL/PRLR is poorly documented. Some years ago, a higher PRLR expression (mRNA level) in various benign mammary diseases compared with normal adjacent tissue has been demonstrated (TOURAINE et al, J Clin Endocrinol Metab 83, 667-674, 1998). A more recent immunohistochemical study confirmed higher PRLR expression in breast tumors (benign and malignant) (GILL et al, J Clin Pathol, 54(12):956-60, 2001). No report of genetic abnormalities (polymorphism, mutation) of the PRLR in benign breast diseases has been published until now.

In order to study a potential relationship between PRL/PRLR and benign breast diseases, the inventors have undertaken to search for polymorphisms in the PRLR gene in patients suffering form such diseases. With this goal, they analyzed patients with multiple fibroadenomas.

Multiple fibroadenomas (also called mammary polyadenomatosis) is a benign mastopathy defined by the presence of more than 3 fibroadenomas in one breast, which occurs generally in young women. Although a hormonal influence has been suggested, the pathophysiology of fibroadenomas and multiple fibroadenomas remains unknown. The former are not considered as premalignant lesions (SANTEN, New England J Med, 353(3):275-85, 2005), and no study investigating whether women presenting with multiple fibroadenomas have an increased relative risk of developing a breast cancer is available.

The analysis of the PRLR gene performed by the inventors in patients presenting with multiple fibroadenomas allowed them to identify 2 missense single nucleotide polymorphisms (SNPs) occurring at a higher frequency in multiple fibroadenoma patients than in control subjects.

One of these SNPs is localized in exon 6 of the PRLR gene. It is a nonsynonymous A to C substitution at position 821 of the PRLR mRNA (GenBank NM_000949), resulting in a mutant prolactin receptor having a Ile (ATT) to Leu (CTT) substitution at position 146 in the polypeptide sequence of the mature form of the receptor (position 170 in the polypeptide sequence of the unprocessed precursor (which is available for instance as Swiss-Prot entry P16471-1).

The other of these SNPs is localized in exon 5 of the PRLR gene. It is a nonsynonymous A to G substitution at position 611 of the PRLR mRNA, resulting in a mutant prolactin receptor having a Ile (ATC) to Val (GTC) substitution at position 76 in the polypeptide sequence of the mature form of the receptor (position 100 in the polypeptide sequence of the unprocessed precursor).

The inventors have further found that these amino acid substitutions generate constitutively active PRLR variants.

As a result of these findings, the present invention provides means for detecting the presence of mutations that result in a constitutive activation of the PRLR, and to study the biological consequences of this activation and its clinical impact on PRL target tissues.

The present invention thus provides a method for detecting whether a subject, preferably a human subject, expresses a constitutively active mutant of the prolactin receptor, wherein said method comprises detecting a mutation in the gene in a nucleic acid sample previously obtained from said subject, said mutation being selected among:

a mutation resulting in the expression of a mutant prolactin receptor wherein the Ile residue at position 146 is substituted by another amino acid residue, preferably by a residue selected among Leu, Met, Thr, Asn, Ser, Phe and Val, and in particular by a Leu residue;

a mutation resulting in the expression of a mutant prolactin receptor wherein the Ile residue at position 76 is substituted by another amino acid residue, preferably by a residue selected among Leu, Met, Thr, Asn, Ser, Phe and Val, and in particular by a Val residue.

These mutations, and the corresponding mutants, will be respectively designated hereinafter as "mutation 146" or "mutant 146" and "mutation 76" or "mutant 76". The particular mutant wherein the Ile residue at position 146 is substituted by a Leu residue will be designated hereinafter as I146L, and the particular mutant wherein the Ile residue at position 76 is substituted by a Val residue will be designated hereinafter as I76V.

The positions indicated herein refer to the sequence of the mature form of the human prolactin receptor (isoform 1), which is represented in the enclosed sequence listing under SEQ ID NO: 1.

A "constitutively active mutant of the prolactin receptor" is herein defined as a mutant of said receptor having a biological activity which is higher than, and is less dependent on prolactin stimulation than the biological activity of the corresponding wild-type receptor.

The I76V mutant has a basal activity which is slightly to moderately higher than the basal activity of the wild-type receptor (depending on the assay used for measuring said activity), while the I146L mutant has a basal activity which is in all assays much higher than the basal activity of the wild-type receptor. As a consequence of their constitutive basal activity, both I76V and the I146L mutants have a fold-stimulation induced by prolactin which is always lower than the fold-stimulation of the wild type receptor.

A broad variety of techniques for detecting SNPs are known in the art (for review, cf. for instance (KWOK, Annu Rev Genomics Hum Genet, 2, 235-258, 2001), and can be used for the detection of the PRLR mutations defined above. Nucleic acid samples suitable for performing the detection include mRNA, cDNA or genomic DNA.

Optionally, the method of the invention may comprise a step wherein the expression of a constitutively active mutant of the PRLR is confirmed by quantifying the activated form of PRLR in a biological sample previously obtained from said subject. This quantification can for instance be performed by measuring the quantity of phosphorylated PRLR with an antibody able to differentiate between the phosphorylated and non-phosphorylated forms of PRLR. This can be performed by immunohistochemical analyses of breast tumor samples obtained from the patients, or by analysis (western blot or other method) of PRLR activation in any cells/tissues (harvested from the patients) which are known to express the PRLR, e.g. lymphocytes (PELLEGRINI et al, Mol Endocrinol, 6, 1023-1031, 1992).

The method of the invention can for instance help to predict the susceptibility of individuals to a disease that involves the PRLR and to decide whether preventive measures against said disease may be taken. In the cases wherein the disease has already set in, it may help to decide of the more appropriate treatment. In particular it may be useful to determine whether a preventive or curative treatment with inhibitors of PRLR signalling cascades (e.g. PRLR antagonists, kinase inhibitors) will be beneficial.

Examples of diseases that involve the PRLR include for instance benign or malignant tumors (hyperplasia, dysplasia, neoplasia, adenoma, carcinoma), dysfunction or developmental failure of PRL target tissues/cells (including but not restricted to breast, prostate, liver, pituitary, pancreas, thyroid, lymphocytes), auto-immune diseases (lupus erythematosus, rheumatoid arthritis), hypermastia, reproduction disorders. The method of the invention allows to determine whether a constitutive activation of the PRLR due to the mutation 76 or the mutation 146 is involved in these diseases.

More specifically, the method of the invention may be helpful for evaluating whether an asymptomatic woman is prone to develop a benign breast disease, in particular multiple fibroadenomas, or whether a woman already presenting with a benign breast disease, in particular a fibroadenoma, is prone to develop multiple fibroadenomas or more aggressive breast diseases (including cancer), and in the case of a woman suffering from these diseases, it may provide useful information to decide on the most appropriate treatment, involving inhibitors of PRLR-triggered signalling cascades such as PRLR antagonists, kinase inhibitors, dopamine agonists or antiestrogens.

The invention also relates to the use of inhibitors of PRLR-triggered signalling cascades, in particular of PRLR antagonists, for preparing a therapeutic composition for treating patients wherein the expression of a constitutively active mutant of the prolactin receptor has been detected by the method of the invention.

The invention provides a method for preventive or curative treatment of a patient wherein the expression of a constitutively active mutant of the prolactin receptor has been detected by the method of the invention, wherein said method comprises administering to said patient a therapeutically effective amount of an inhibitor of a PRLR-triggered signalling cascade, in particular a PRLR antagonist.

PRLR antagonists are known in themselves (for review, cf. (GOFFIN et al., Endocr Rev, 26, 400-422, 2005). Examples of PRLR antagonists that can be used in the therapeutic method of the invention include those disclosed in PCT WO03/057729, which are variants of prolactin having mutations preventing the formation of the disulfide bridge between $Cys_4$ and $Cys_{11}$, and inducing steric hindrance within binding site 2 of prolactin.

The invention also provides the isolated mutant 146 or mutant 76 defined above, or the unprocessed precursors thereof, as well as isolated polynucleotides encoding said mutant 146 and mutant 76, or said precursors. The invention further provides host-cells, as well as non-human mammals, for instance mice, which have been genetically modified by a polynucleotide of the invention, and which express the mutant 146 and/or the mutant 76. This includes in particular transgenic mammals, containing a transgene expressing the desired mutant PRLR, as well as knock-in mammals, wherein the desired mutation has been introduced in the endogenous PRLR gene (for instance by homologous recombination).

These genetically modified host cells and non-human mammals of the invention are useful in particular for studying the biological and pathophysiological effects of the constitutive activation of the PRLR.

The present invention will be further illustrated by the additional description which follows, which refers to examples illustrating the demonstration of the biological properties of the I146L or I76V mutants. It should be understood however that these examples are given only by way of illustration of the invention and do not constitute in any way a limitation thereof.

EXAMPLE 1

Figure 1:
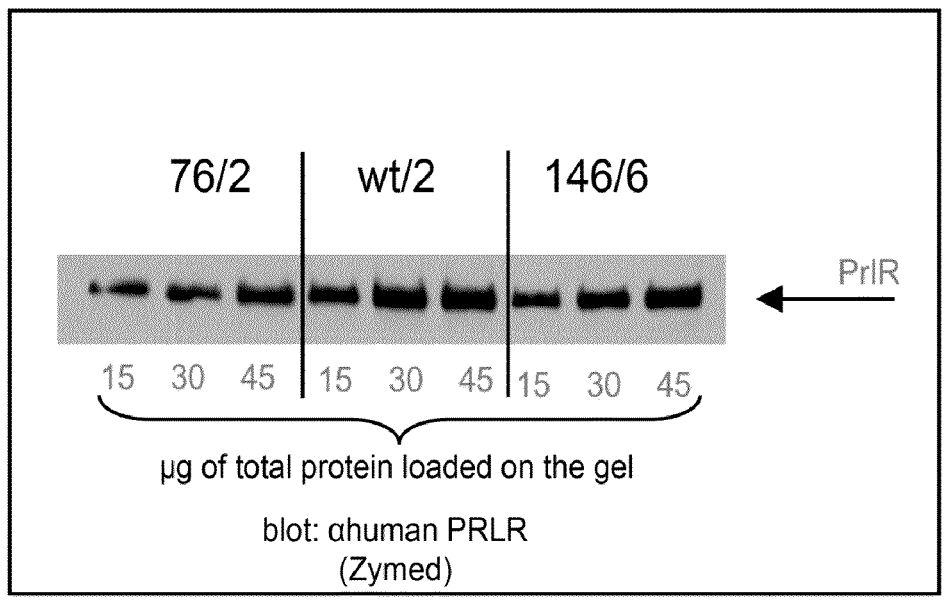
FIG. 1 illustrates analysis of 3 selected clones (76/2, WT/2 and 146/6) by semi-quantitative western blot with anti-human PRLR expressing similar amounts of the human PRLR (WT or mutated) for comparison of mutants versus WT PRLR.

Identification of Mutations in the PRLR Gene of Patients with Multiple Fibroadenoma 77 patients with multiple fibroadenoma and 66 control subjects were analyzed for mutations in the 11 exons of the PRLR gene.

A mutation in Exon 5, resulting in the expression of a mutant prolactin receptor having a Ile to Val substitution at position 76 of the sequence of the mature form of the prolactin receptor was found in 9 patients with multiple fibroadenomas and in 3 control subjects.

A mutation in Exon 6 resulting in the expression of a mutant prolactin receptor having a Ile to Leu substitution at position 146 of the sequence of the mature form of the prolactin receptor was found in 4 patients with multiple fibroadenomas and in none of the control subjects.

EXAMPLE 2

Construction of Expression Vectors for the PRLR Variants

Receptor Constructs

The human PRLR cDNA inserted into the pc/DNA3 eukaryotic vector (InVitrogen, Carlsbad, Calif.) has been generated as described previously (LOCHNAN et al, Mol Cell Endocrinol 114:91-99, 1995; GOFFIN et al, J Biol Chem 271:16573-16579, 1996). The PRLR-responsive LHRE-luciferase reporter gene carries the sequence encoding the firefly luciferase gene under the control of a 6-repeat sequence of the lactogenic hormone response element (LHRE) followed by the minimal thymidine kinase promoter (GOFFIN et al., J Biol Chem, 271, 16573-16579, 1996). LHRE is the DNA binding element of the signal transducer and activator of transcription Stat5, one of the signaling proteins activated by the PRLR once it is activated (WAKAO et al, EMBO J. 13, 2182-2191, 1994).

Site Directed Mutauenesis

Construction of the mutated hPRLR cDNA encoding I76V and I146L was performed by oligonucleotide-directed mutagenesis method using the QuikChange II Mutagenesis kit from Stratagene (La Jolla, Calif.), strictly following the manufacturer's instructions. We used the following mutated oligonucleotides:

```
Forward I76V:
gtggaggacatacgtcatgatggtcaatgcc       (SEQ ID NO: 2)

Reverse I76V:
ggcattgaccatcatgacgtatgtcctccac       (SEQ ID NO: 3)

Forward I146L:
cgctcctgtatgaacttcgattaaaacccg        (SEQ ID NO: 4)

Reverse I146L:
cgggttttaatcgaagttcatacaggagcg        (SEQ ID NO: 5)
```

Mutated plasmids were sequenced on both strands to confirm the presence of the mutations of interest and the absence of unexpected mutations.

EXAMPLE 3

Functional Assays of the PRLR Variants in HEK 293 Host-Cells

Transient and Stable Transfections

We used the human embryonic kidney (HEK) fibroblast 293 cell line to study the functionality of mutated PRLR, either via transient transfection or using clonal cell lines stably expressing the hPRLR of interest (WT, I76V and I146L), as previously described (GOFFIN et al., J Biol Chem, 271, 16573-16579, 1996; KINET et al., J Biol Chem, 274, 26033-26043, 1999; LEBRUN et al., Proc Natl Acad Sci USA, 92, 4031-4035, 1995).

Cells were routinely cultured in DMEM medium supplemented with 10% FCS, 2 mM glutamine, 50 U/mL penicillin, 50 µg/mL streptomycin. Cells were co-transfected, using the lipofectamine method with two or three plasmids, one encoding the receptor of interest, one encoding the LHRE-firefly luciferase vector as a reporter of PRLR-mediated a effects, and one encoding the *Renilla* Luciferase which is expressed in a PRL-independent manner and serves as an internal control of transfection efficiency (DOS SANTOS et al., Nat Genet, 36, 720-724, 2004).

For experiments involving transient transfections, cells were used 24-48 hours after transfection. For the generation of stable clones, cells were shifted to growth medium containing 500 µg/mL active G-418 (geneticin) 24-48 hours after transfection for clonal selection. From this step, G-418 was systematically added to all culture media. After 15 to 20 days, single G-418 resistant colonies were localized by microscope, picked out individually by local trypsinization and amplified in 24-well plates before being characterized for their ability to respond to hPRL as monitored by the induction of luciferase activity.

Stable clones were analyzed by semi-quantitative western blot with anti-human PRLR in order to select clones expressing similar amounts of the human PRLR (WT or mutated) for comparison of mutants versus WT PRLR. As examples, the results for 3 selected clones (76/2, WT/2 and 146/6) are shown on FIG. 1.

Binding affinities of mutated PRLR for hPRL were determined using cell homogenates of stably transfected HEK 293, following a procedure previously described (KINET et al., J Biol Chem, 274, 26033-26043, 1999). Briefly, recombinant hPRL, produced in bacteria *E. coli* using the pT7L expression vector, and purified as described previously (PARIS et al., Biotechnol Appl Biochem, 12, 436-449, 1990), was iodinated using the Iodogen method, and its specific activity was in the range of 4-5 µCi/µg. Binding assays were performed overnight at room temperature using 150-300 µg cell homogenate protein in the presence of 20,000-30,000 cpm $[^{125}I]$-hPRL and increasing concentrations of unlabeled hPRL (competitor). Scatchard analysis was performed to determine the binding affinity of mutated PRLR and the number of PRLR per cell in stable clones or populations.

Figure 2:
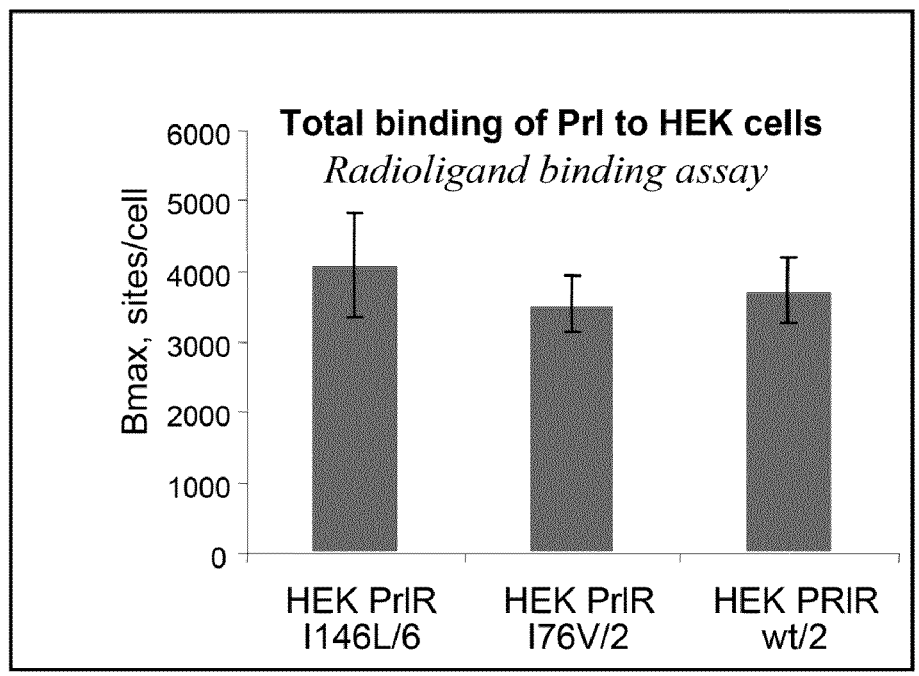
FIG. 2 illustrates that the 3 selected clones 76/2, WT/2 and 146/6 have a similar number of PRLR per cell.

FIG. 2 shows that the 3 selected clones 76/2, WT/2 and 146/6 have a similar number of PRLR per cell.

Figure 3:
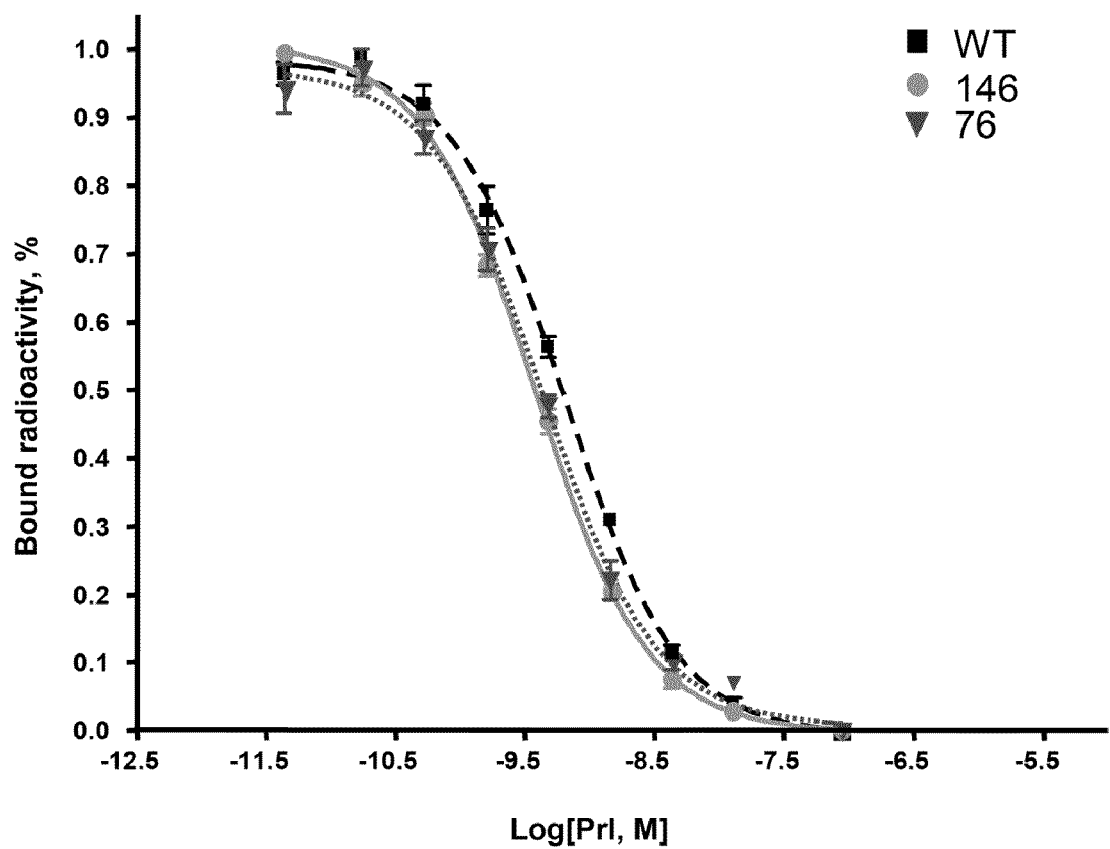
FIG. 3 illustrates that the binding affinity for hPRL is unchanged by the mutation. The Kd for the wild-type PRLR is of 0.64 nM, the Kd for the I146L mutant is of 0.38 nM, and the Kd for the I76V mutant is of 0.44 nM.

FIG. 3 shows that the binding affinity for hPRL is unchanged by the mutation. The Kd for the wild-type PRLR is of 0.64 nM, the Kd for the I146L mutant is of 0.38 nM, and the Kd for the I76V mutant is of 0.44 nM Similarly, the affinity for the pure PRLR antagonist Del1-9-G129R-hPRL (BERNICHTEIN et al., J Biol Chem, 278, 35988-35999, 2003) is also identical for the mutants and the receptors (not shown).

LHRE-Luciferase Reporter Assay

After trypsinization, cells were counted and aliquoted in 96-well plates at a density of 50,000 cells/100 µL/well. Plating medium contained 0.5% FCS to allow cell adhesion. Six to eighteen hours (overnight) after plating, cells were stimulated by addition to each well of 100 µL of PRL (1 µg/ml) diluted in FCS-free medium. After 24 hours of stimulation, culture medium was aspirated and cells were lyzed for at least 10 minutes in 50-100 µL of lysis buffer (Promega). Luciferase activity (only firefly luciferase for stable clones, and both firefly and renilla luciferases for transient transfections) for each experimental condition was counted in 10-20 µL of cell lysates for 10 seconds using a luminometer (Lumat LB 9501, Berthold, Nashua, N.H.). Dual-Glo luciferase kit (Promega) was used for measuring firely and renilla luciferases in the same sample for transient transfections. The difference between duplicates never exceeded 15% of RLU values. Although the latter were found to slightly decrease along cell passages, this did not significantly affect the fold induction of luciferase activity (calculated as the ratio between the RLU of stimulated vs non stimulated cells) which always remained around 10 or higher.

Figure 4:
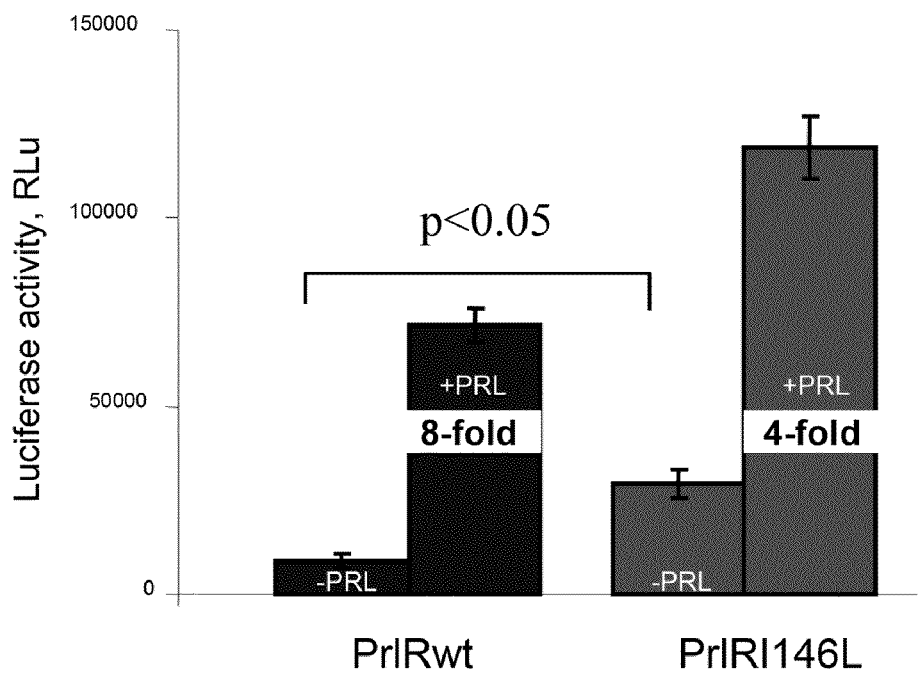
FIG. 4 illustrates that basal activity (unstimulated cells) is much higher in cells expressing PRLR mutant I146L compared to WT receptor. Hence, the fold stimulation induced by PRL is lower (4 fold versus 8 fold).

The results, illustrated by FIG. 4 show that basal activity (unstimulated cells) is much higher in cells expressing PRLR mutant I146L compared to WT receptor. Hence, the fold stimulation induced by PRL is lower (4 fold versus 8 fold).

Figure 5:
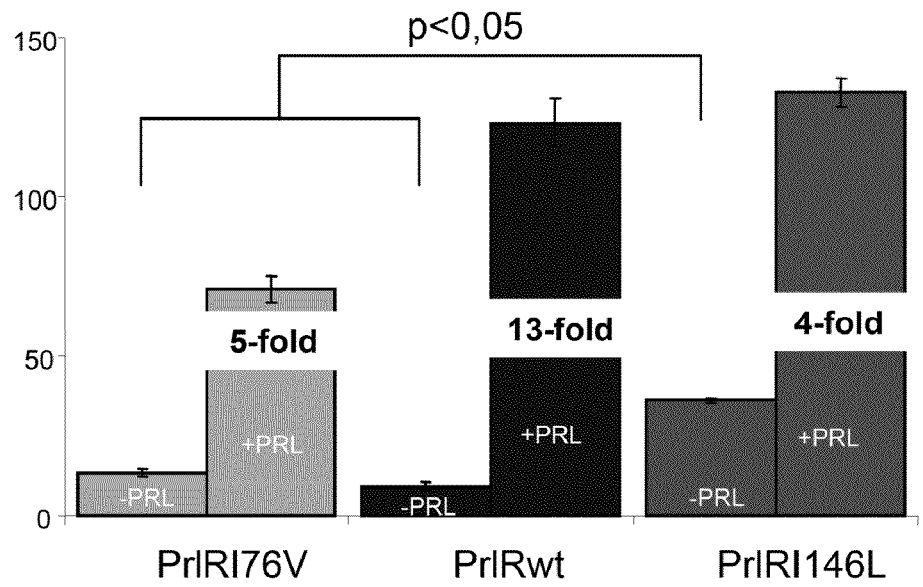
FIG. 5 illustrates the results obtained from transient transfections and the results expressed as normalized values (ratio of firefly luciferase versus renilla luciferase).

The same experiment was repeated in transient transfections with similar observations. The results shown in FIG. 5 were obtained in transient transfections and are expressed as normalized values (ratio of firefly luciferase versus renilla luciferase). They confirm the data shown in FIG. 4, which indicates that this is not an artifact of stable clones. For I76V mutant, basal activity is similar to WT, but fold induction (5 fold) is similar to I146L mutant. This suggests that the constitutive activity of I76V mutant is lower than that of I146L mutant.

Analysis of PRLR Phosphorylation by Immunoprecipitation and Western Blot

Receptor phosphorylation on tyrosine residues is the first step of PRLR activation. Since the luciferase assay indicates higher basal activity for I146L mutant, we analyzed receptor phosphorylation by immunoprecipitation and western blot, as previously described (LLOVERA et al., Oncogene, 19, 4695-4705, 2000).

Transient or stable transfected cells were starved overnight in FCS-free medium before hormonal stimulation. The next day, cells were stimulated (5-30 min at 37° C.) using various concentrations of WT hPRL as indicated. At the end of the stimulation, cells were washed twice with ice-cold saline buffer and cell pellets were kept frozen until used. Cells were solubilized in 0.5-1 ml lysis buffer (30 min under gentle rotation at 4° C.). Lysates were centrifuged for 10 min at 13,000×g, then supernatants were quantified for their protein content by Bradford assay and used for immunoprecipitation.

For immunoprecipitation studies, 0.5-1 mg of total lysate were incubated with anti-human PRLR (anti extracellular domain of the human PRLR, Zymed, clone 1A2B1), used at 1-5 µl/ml. After overnight rotation at 4° C., immune complexes were captured using 20 µl Protein A Sepharose slurry for 1 additional hour rotation at 4° C. Protein A complexes were precipitated by centrifugation, pellets were washed 3 times in lysis buffer and boiled in 15 µl reducing SDS sample buffer for 5 min at 95° C. Finally, immunoprecipitated samples were analysed using 7.5% SDS-PAGE. Electrophoretic transfer onto nitrocellulose membranes (Bio-Rad) was performed as described (LLOVERA et al., Oncogene, 19, 4695-4705, 2000). Membranes were blocked with 5% skimmed milk or BSA buffer, in Tris-buffered saline-Tween 20 (TBST) for 2 hours at room temperature. After washing in TBST, they were incubated overnight (4° C.) in 3% BSA/TBST containing 4G10 anti-phosphotyrosine antibody (UBI, 1:10,000 dilution). Membranes were again washed in TBST and incubated for 1 hour (RT) with 1:4,000 dilution of horseradish peroxidase conjugated anti-mouse or anti-rabbit antibody (Amersham Pharmacia Biotech). After washing, immunoblots were revealed by 1 min ECL reaction (Enhanced Chemiluminescence detecting reagents, GE Healthcare, UK) followed by autoradiography (various exposure times). When required, the membranes were stripped and re-incubated with anti-human PRLR antibody.

Figure 6:
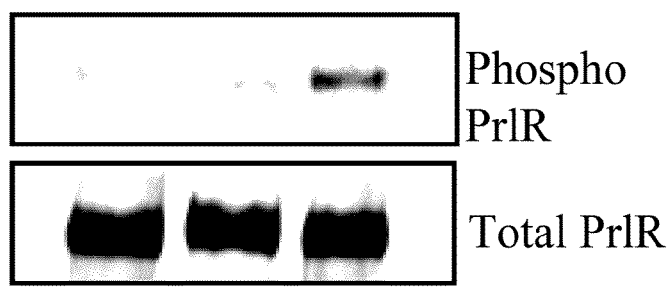
FIG. 6 shows the I146L mutant is constitutively phosphorylated in the absence of PRL stimulation in a stable clone.

As shown on FIG. 6, I146L mutant is constitutively phosphorylated in the absence of PRL stimulation in a stable clone. This was also observed in stable populations (=pool of non purified stable clones) and transient transfections (not shown). This indicates that it is an intrinsic property of the mutated receptor.

Figure 7:
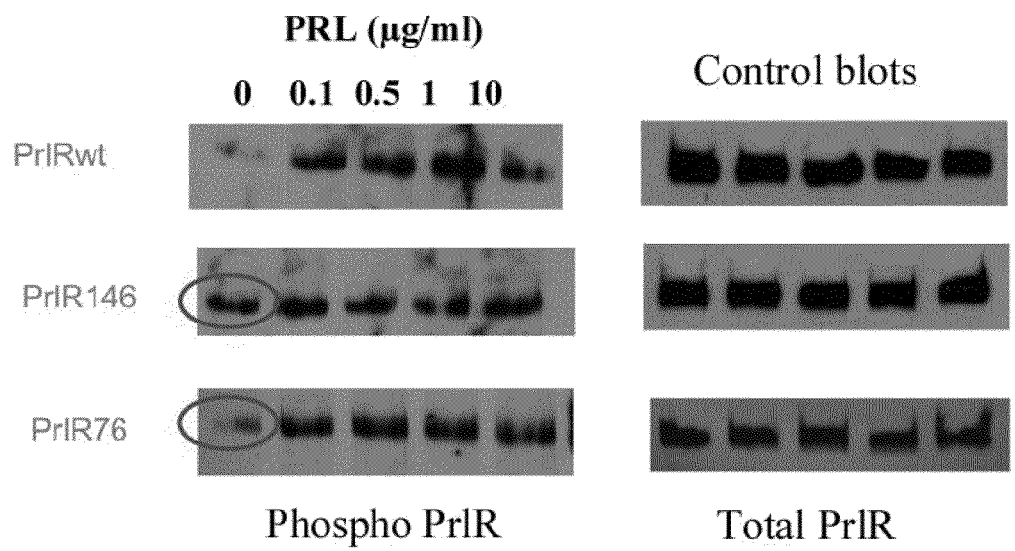
FIG. 7 shows constitutive phosphorylation of mutant I76V as weaker in this cell system and as a consequence, PRL stimulation increased phosphorylation of PRLR mutant I76V.

In contrast, constitutive phosphorylation of mutant I76V was weaker in this cell system (FIG. 7, bottom left). As a consequence, PRL stimulation increased phosphorylation of PRLR mutant I76V, while it had no detectable effect for mutant I146L.

Effect of PRLR inhibitors:

The effect of two known inhibitors of PRLR/JAK2/Stat5 signalling were tested using the LHRE-luciferase assay and the PRLR phosphorylation assay. The two inhibitors tested are the pure PRLR antagonist Del1-9-G129R-hPRL, which interferes with the mechanism of receptor activation by PRL (BERNICHTEIN et al., J Biol Chem, 278, 35988-35999, 2003) and Tyrphostin AG490 (N-Benzyl-3,4-dihydroxy-benzylidenecyanoacetamide), a classical inhibitor of JAK2 activity, the PRLR-associated kinase.

The LHRE-luciferase assay and the PRLR phosphorylation assay were performed as disclosed above, except that the cells were incubated with or without (basal receptor activity) various concentrations of Del1-9-G129R-hPRL or of AG490 for the LHRE-luciferase assay, and with 20 µg/ml of Del1-9-G129R-hPRL or 50 mM of AG490 for the PRLR phosphorylation assay (both WT and mutated receptor tested in parallel). No PRL was added in any condition.

Figure 8:
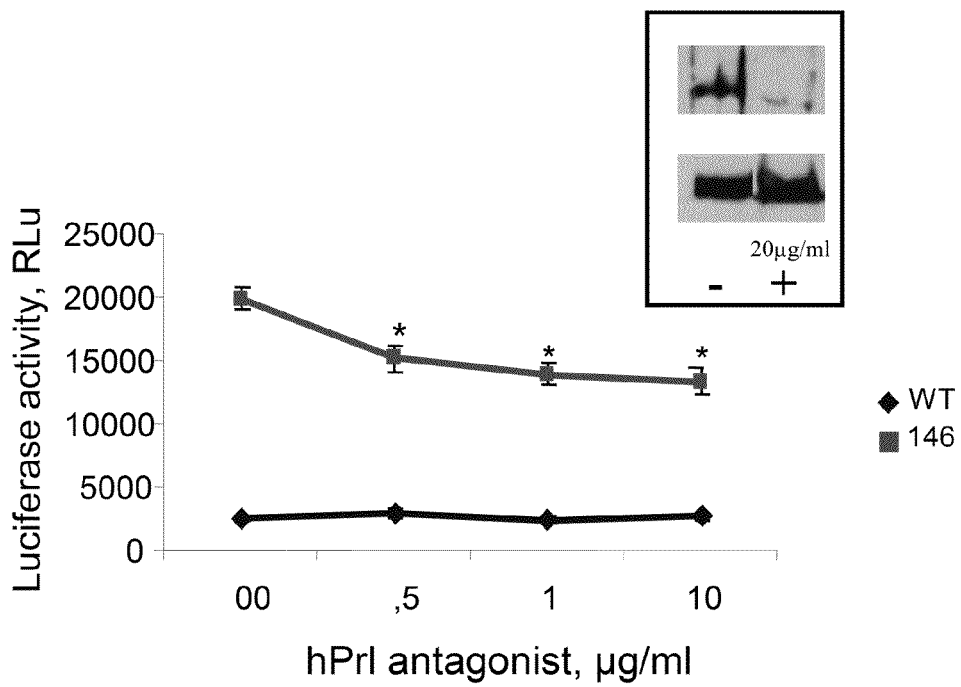
FIG. 8 illustrates LHRE-luciferase assay and the PRLR phosphorylation assays performed as with the cells being incubated with or without (basal receptor activity) various concentrations of Del1-9-G129R-hPRL.
Figure 9:
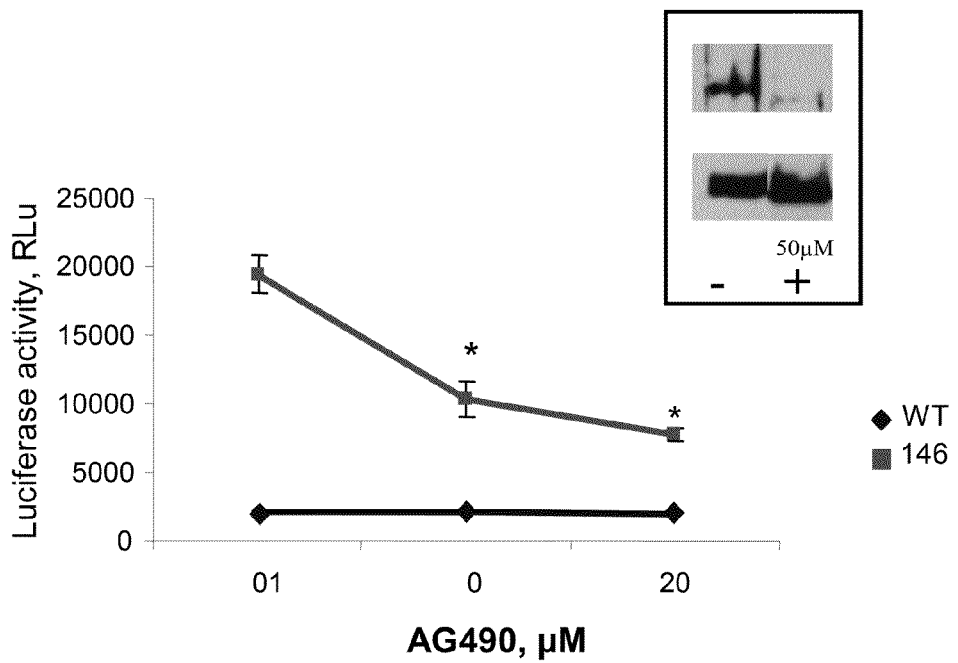
FIG. 9 illustrates LHRE-luciferase assay and the PRLR phosphorylation assays performed as with the cells being incubated with or without (basal receptor activity) various concentrations of AG490.

The results are illustrated by in FIG. 8 for Del1-9-G129R-hPRL and FIG. 9 for AG490.

These results show that constitutive signaling of mutant I146L to LHRE promoter in the absence of PRL stimulation is partially inhibited by both inhibitors. As expected, the wild-type PRLR used as a control is devoid of activity, independently of the concentration of inhibitor.

The effects of the two inhibitors on receptor phosphorylation are shown in the top blots of insets of FIGS. 8 and 9 (the bottom blots representing total PRLR). In both cases, inhibition of receptor phosphorylation parallels inhibition of luciferase activity.

These results clearly indicate that the constitutive activation of these responses in mutant I146L is PRLR-dependent, and that it can be partially inhibited by inhibitors such as PRLR antagonists.

EXAMPLE 4

Functional Assays of the PRLR Variants in BA/F3 Host-Cells

Ba/F3 cells were chosen for further experiments since it has been previously show that they represent a more sensitive model which is more able to detect moderate/low activities than HEK 293 cells (BERNICHTEIN et al., Endocrine, 20, 177-190, 2003).

Ba/F3 cells are a pro-B murine cell line dependent on IL-3 for growth. Cells were transfected by electroporation using 5-20 µg of plasmid encoding the WT or mutated human PRLR(CMV promoter), then the populations stably expressing the receptor was selected by several passages in G418-containing medium. Ba/F3-hPRLR cells were routinely maintained in RPMI 1640 medium supplemented with 10% heat-inactivated FCS, 2 mM glutamine, 50 U/mL penicillin, 50 µg/mL streptomycin, 700 µg/mL G-418 (for selection of stably transfected cells), and 10-100 ng/mL WT hPRL instead of IL-3 as the growth factor.

In the same way as described in Example 3 for HEK 293 cells, Scatchard analysis was performed to determine the level of PRLR expression in the stable populations.

Figure 10:
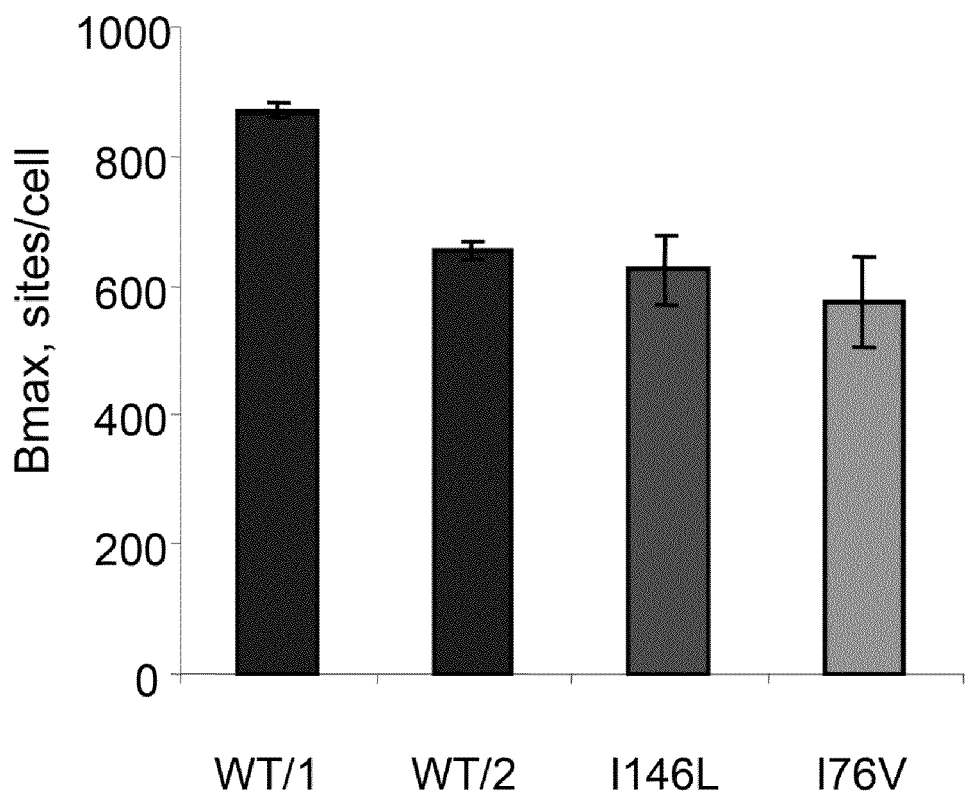
FIG. 10 illustrates Scatchard analysis performed to determine the level of PRLR expression in the stable population.

The results are shown in FIG. 10.

As shown here, all populations generated for comparing receptor properties (2 for WT, 1 for each mutant) expressed similar amounts of receptor. The level of PRLR expression is by far lower than in stable HEK clones (FIG. 2).

Proliferation Assays

Cells were starved for 6 hours in 1% FCS RPMI medium with additives (no PRL), then distributed in 96 well-plates at a density of $5\times10^4$ cells/well in a final volume of 100 µL. One hundred µL, of [2×] hPRL (and/or antagonist) diluted in the same medium were added after starvation period. Cell survival/proliferation was estimated after 2-3 days of hormonal stimulation by adding 10-20 µL, of WST-1 tetrazolium salt, which is metabolized by living cells (BERNICHTEIN et al., Endocrine, 20, 177-190, 2003). Optical density at 450 nm ($OD_{450}$) was measured after 1-3 hours of colorimetric reaction using an ELISA plate reader. The experiments were routinely performed at least three times in triplicate or quadruplicate.

Proliferation of Ba/F3Cells Expressing the WT PRLR or the I146L or I76V Mutant

Figure 11:
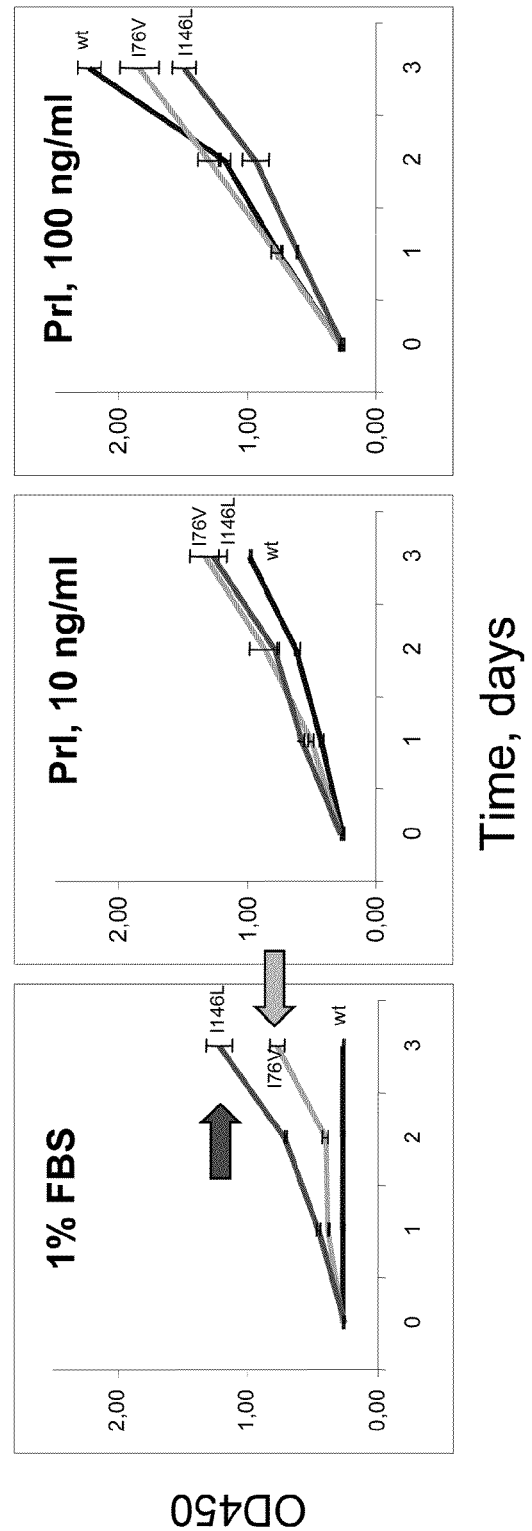
FIG. 11 shows the results of experiences performed with Ba/F3 cells grown in 96 wells plates, in poor medium (1% FCS), with 0 (left panel), 10 (medium panel) or 100 (right panel) ng/ml hPRL.

FIG. 11 shows the results of experiences performed with Ba/F3 cells grown in 96 wells plates, in poor medium (1% FCS), with 0 (left panel), 10 (medium panel) or 100 (right panel) ng/ml hPRL.

In the absence of PRL, cells expressing WT PRLR hardly survived. Mutant I76V exhibited moderate but significant constitutive proliferation, while mutant I146L exhibited proliferation similar to that induced by PRL on cells expressing WT PRLR. PRL did not markedly influence proliferation of I146L mutant population, while it further increased that of I76V mutant population.

Effect of PRLR Inhibitors on Proliferation of Ba/F3Cells Expressing the Wt PRLR or the I146L or I76V Mutant Proliferation of stable Ba/F3 cell populations was evaluated in poor medium (1% FCS) in the presence of WT hPRL, or of the PRLR antagonist Del1-9-G129R-hPRL, or of AG490, for 3 days. The results are illustrated in FIGS. 12 and 13.

Figure 12:
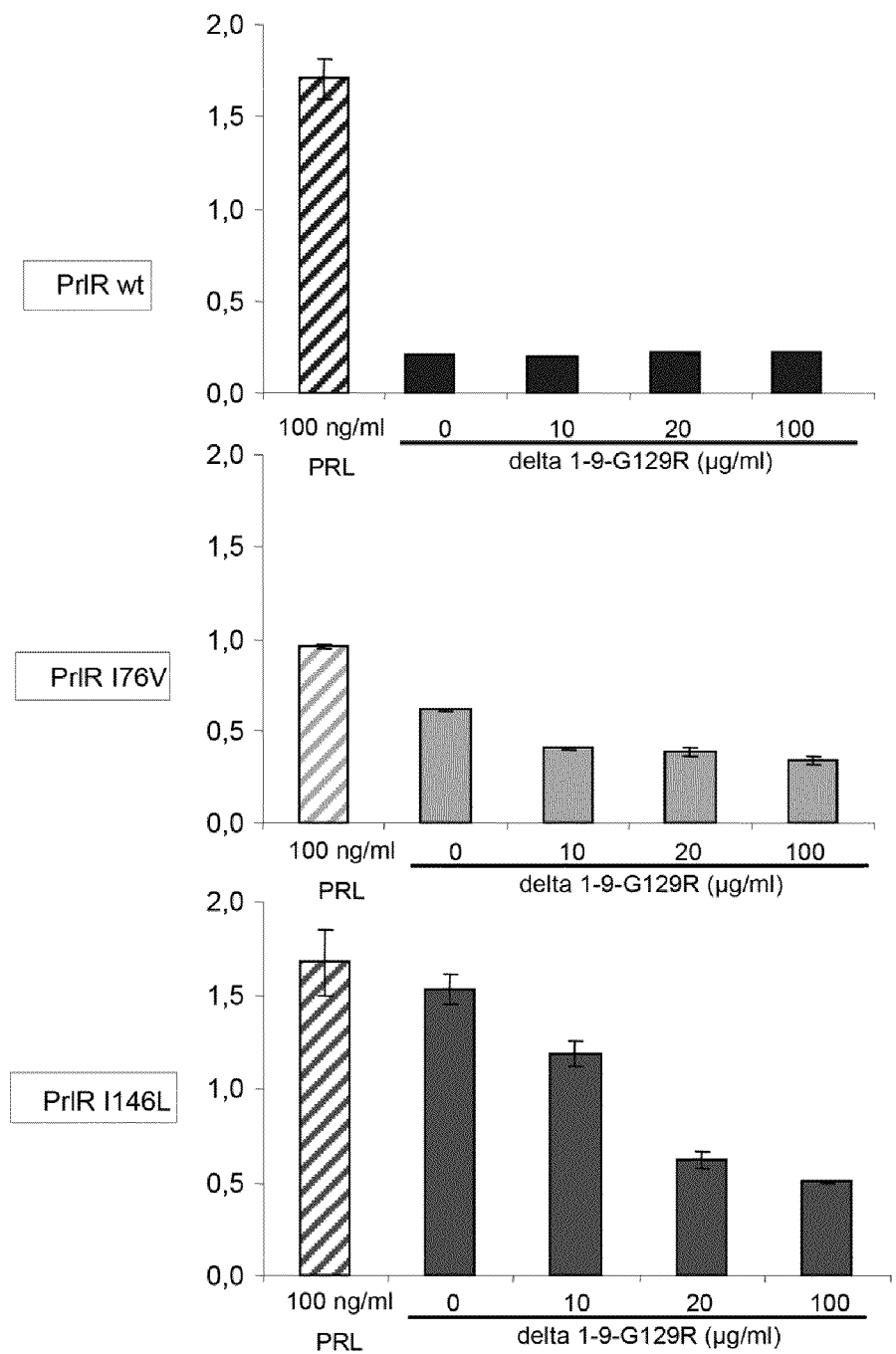
FIG. 12 illustrates that the antagonist Del1-9-G129R-hPRL has no effect on basal proliferation (no PRL) of WT PRLR cells (top panel), indicating the absence of toxic effect.

FIG. 12 shows clearly that the antagonist Del1-9-G129R-hPRL has no effect on basal proliferation (no PRL) of WT PRLR cells (top panel), indicating the absence of toxic effect. In contrast, the moderate constitutive activation of mutant I76V (middle panel, second bar) is inhibited by 10 µg/ml antagonist (middle panel, third and further bars). A dose-dependent effect is also very clear for inhibition of the strong constitutive activity of mutant I146L (bottom panel, second and further bars). These results show that constitutive proliferation is PRLR-specific/dependent, and that the antagonist Del1-9-G129R-hPRL is potentially an interesting way to inhibit the constitutive activity of these mutants.

Figure 13:
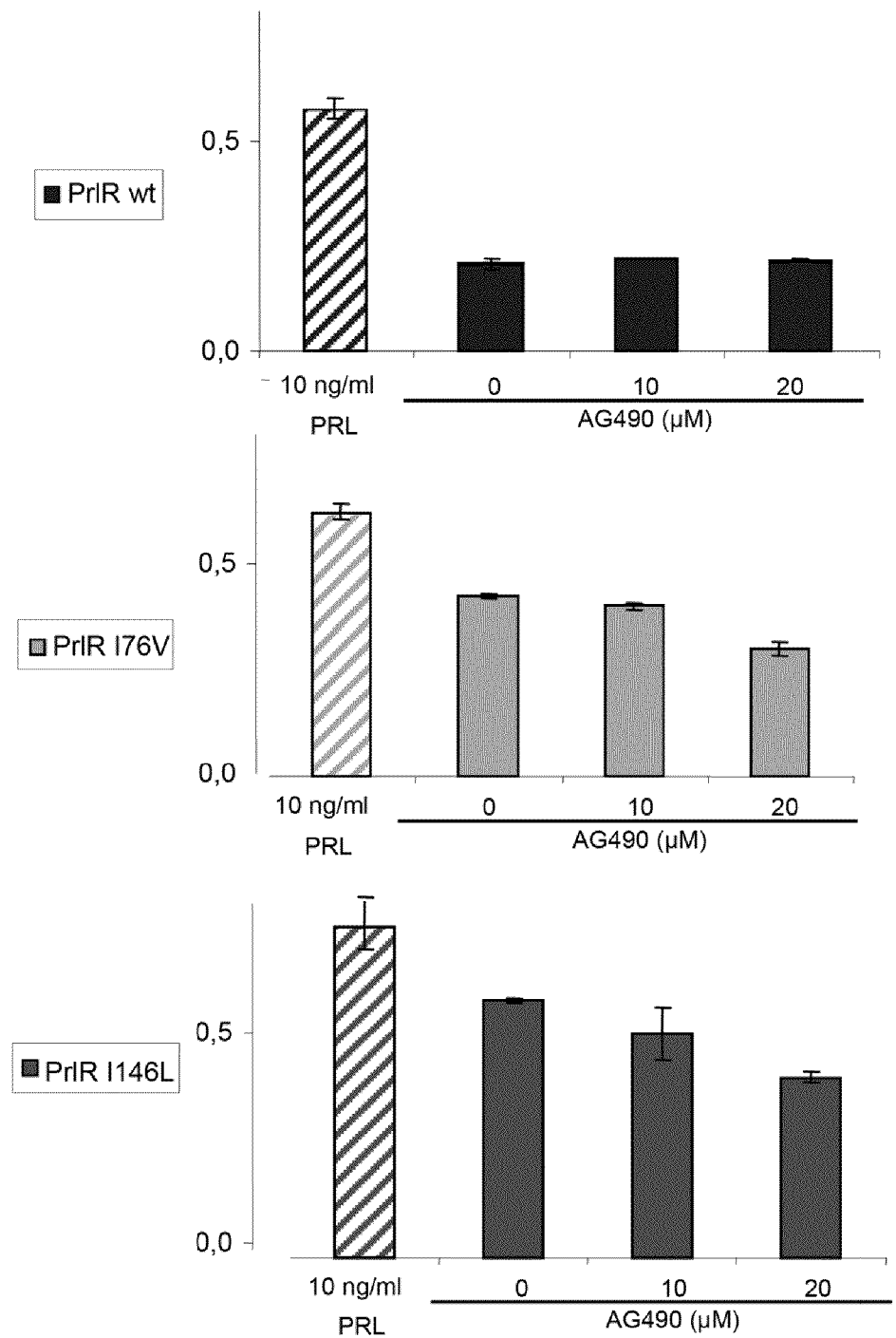
FIG. 13 illustrates that AG490 has no effect on basal proliferation (no PRL) of WT PRLR cells (top panel), indicating the absence of toxic effect.

In the same way, FIG. 13 shows clearly that AG490 has no effect on basal proliferation (no PRL) of WT PRLR cells (top panel), indicating the absence of toxic effect. In contrast, the moderate constitutive activation of mutant I76V (middle panel, second bar) was partially inhibited by 20 µM AG490 (middle panel, third and fourth bars). A dose-dependent effect is also observed for inhibition of the strong constitutive activity of mutant 146 (bottom panel, second and further bars). These results show that constitutive proliferation is PRLR/JAK2 signaling-dependent, and that kinase inhibitors are potentially an interesting way to inhibit constitutive activity of these mutants.

Anti-Apoptotic Effect of PRLR Mutants

The cell cycle of transfected Ba/F cells (stable populations) was studied by FACS analysis, using propidium iodine labelling as previously described (JEAY et al., Endocrinology 142:147-156, 2001). Cells were put in minimal medium, with or without PRL for the indicated time.

Figure 14:
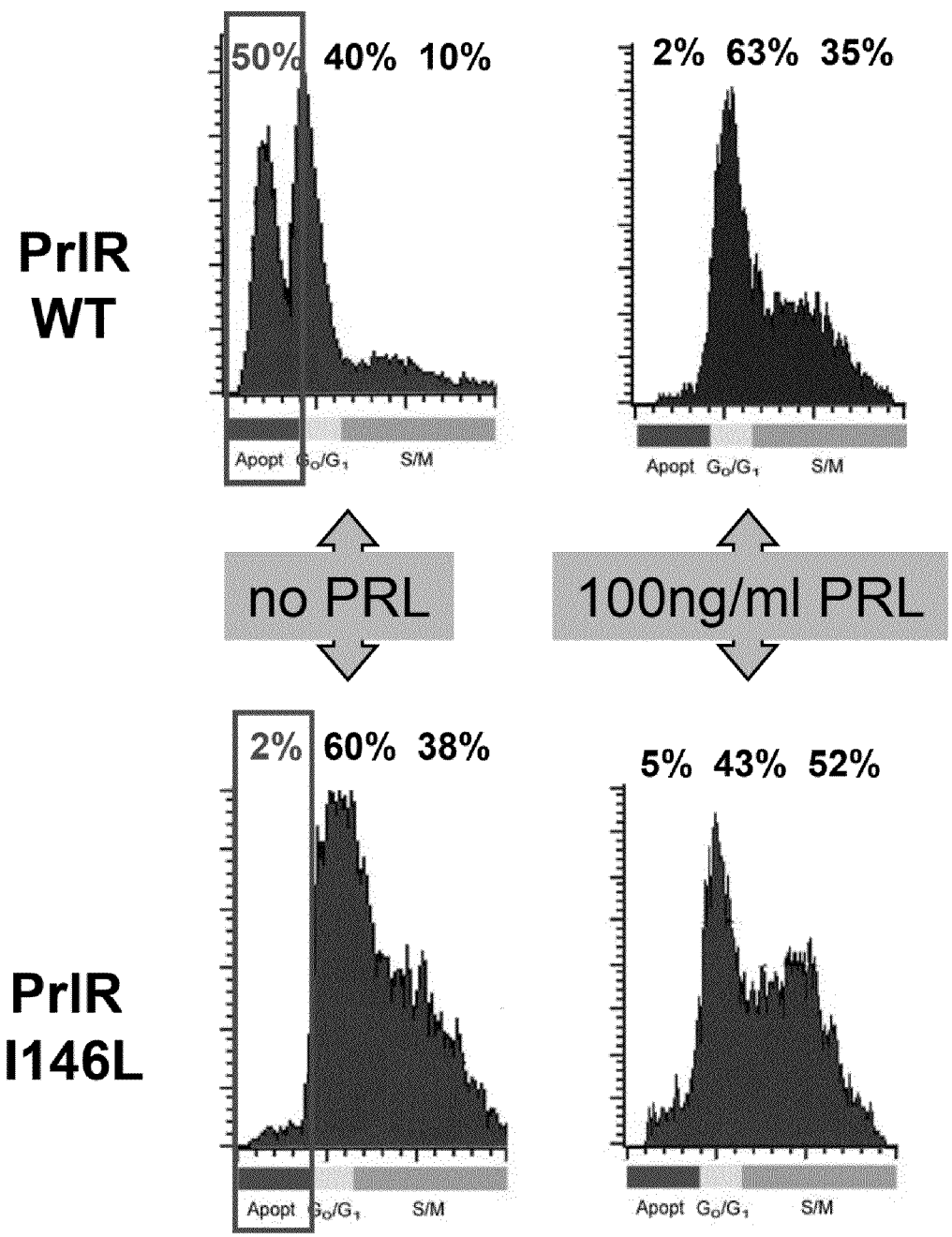
FIG. 14 illustrates that in the absence of PRL, cells expressing WT PRLR undergo rapid apoptosis (50%) in 30 h. PRL prevents this effect. In sharp contrast, cells expressing mutant I146L never undergo apoptosis even without PRL. This clearly indicates that cells cycle all the time irrespective of PRL stimulation. The same result was observed for mutant I76V.

The results are illustrated by FIG. 14. In the absence of PRL, cells expressing WT PRLR undergo rapid apoptosis (50%) in 30 h. PRL prevents this effect. In sharp contrast, cells expressing mutant I146L never undergo apoptosis even without PRL. This clearly indicates that cells cycle all the time irrespective of PRL stimulation (FIG. 14). The same result was observed for mutant I76V.

Figure 15:
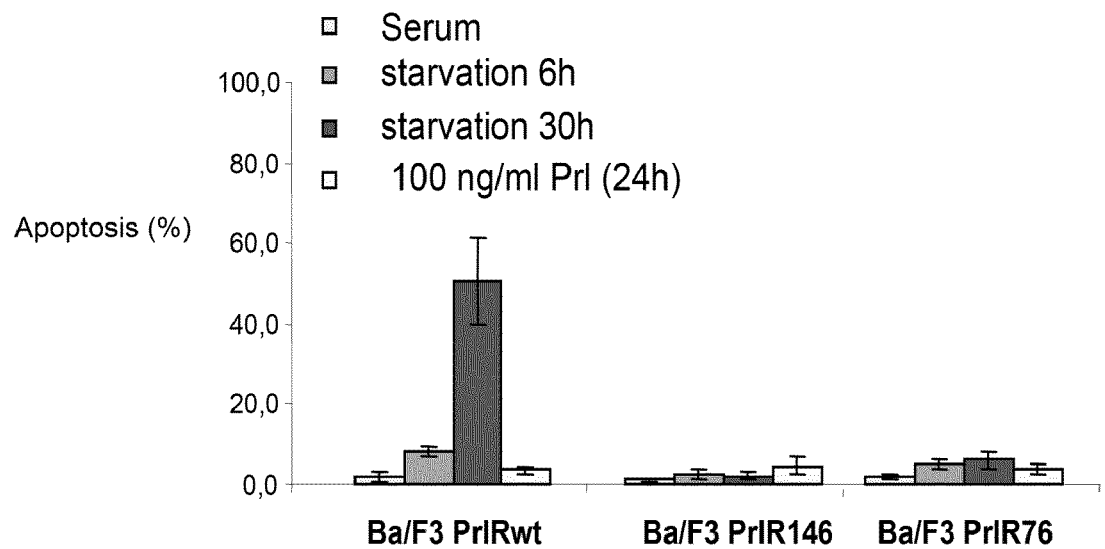
FIG. 15 illustrates the anti-apoptotic effect of both mutants in comparison to WT PRLR, at various time points.

FIG. 15 summarizes the anti-apoptotic effect of both mutants in comparison to WT PRLR, at various time points. Effect of the I146L or the I76V Mutation on Phosphorylation of Stat5.

Stat5 is the main PRLR signalling mediator, and a known anti-apoptotic factor in Baf cells. Its phosphorylation was analyzed by immunoprecipitation and western blot, using the protocol described in Example 3 for the analysis of PRLR phosphorylation.

Immunoprecipitation was performed with anti-STAT5 antibodies (c17, SantaCruz). The membranes were incubated with anti-PY antibody (4G10, Upstate), and when required re-incubated with anti-STAT5 (c17, SantaCruz) antibodies.

Figure 16:
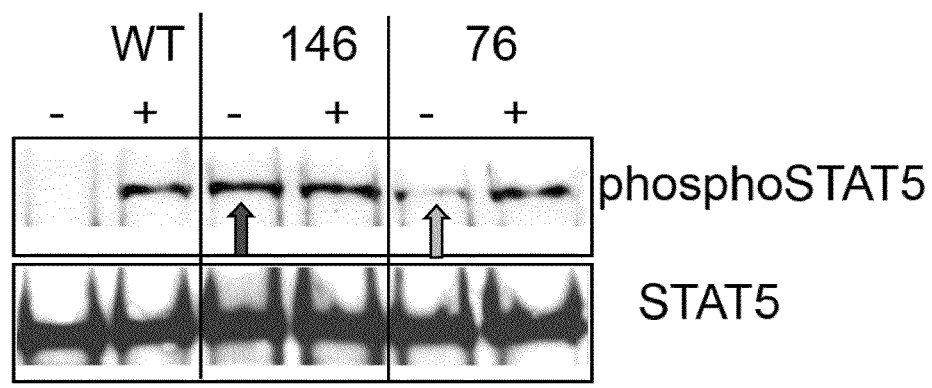
FIG. 16 illustrates that in the absence of PRL stimulation, a strong phosphorylation of Stat5 occurs in populations expressing I146L mutant. The phosphorylation of Stat5 in I76V mutant is moderate, and can be increased by PRL stimulation.

The results are illustrated by FIG. 16: (−)=no PRL, (+)=0,5 µg/ml PRL.

These results show that in the absence of PRL stimulation, a strong phosphorylation of Stat5 occurs in populations expressing I146L mutant. The phosphorylation of Stat5 in I76V mutant is moderate, and can be increased by PRL stimulation. These effects are in perfect agreement with the data obtained in proliferation assays (cf. FIG. 11).

In conclusion, the above results show that Mutant I146L is constitutively active in both transfected cell systems. This is demonstrated by constitutive tyrosine phosphorylation of the receptor and constitutive activation of JAK2-Stat5 pathway, which results in transcription of target genes (LHRE as a model), proliferation and/or anti-apoptotic effects. Receptor antagonists and JAK2 inhibitors confirm the specificity of these observations.

In both systems, the constitutive activity of mutant I146L is clearly stronger than that of mutant I76V. For the latter, it is weak in HEK cells, while it is intermediate in BaF cells (i.e. somewhere between non simulated and PRL-stimulated cells expressing WT PRLR).

The cell systems used in this study involve the homologous (human) PRLR. As such, they were previously used to characterize the biological activity of hPRL isoforms with pathophysiological relevance (namely macroprolactin). No significant biological activity could be detected for macroprolactin, in agreement with the absence of symptoms of hyperprolactinemia in these patients (GLEZER A et al, J Clin Endocrinol Metab 91:1048-1055, 2006; LEANOS-MIRANDA et al, Clin Endocrinol (Oxf) 65:146-153, 2006). In addition, we previously showed that the Baf cells exhibit a sensitivity closer to physiological conditions (GOFFIN et al., Endocr Rev, 26, 400-422, 2005). Therefore, it can be considered that the constitutive activity of both I76V and I146L mutants demonstrated in these cells closely reflects the activity in vivo, which should have pathophysiological impact.

EXAMPLE 5

Test for Detecting the I146L and I76V Mutations

Primers for PCR reactions were designed in intronic regions bordering human PRLR exons 5 and 6, using published DNA sequences (NCBI web site, DNA sequence of PRLR gene: NT_006576). Primer sequences are the following:

```
Exon 5:
Forward:  ccagtggtattgatctatga    (SEQ ID NO: 6)

Reverse:  gtaagaaattcctcacccac    (SEQ ID NO: 7)
Annealing T°: 52° C.

Exon 6
Forward:  aaaggtgcaagcaatgagtg    (SEQ ID NO: 8)

Reverse:  ccaacacagtgacccagtaa    (SEQ ID NO: 9)
Annealing T°: 56° C.
```

PCR amplifications were performed in a PTC-100 thermocycler (MJ Research Inc.) in a final volume of 50 µl using 50-100 ng of DNA.

PCR products were then checked for size by agarose gels, and mutated receptor DNAs were then identified by restriction enzymes (Fermantas-Euromedex):

Exon 5 PCR products (285 bp) were digested by TaiI (MaeII) for 2 h at 65° C. There is one restriction site in the PCR product amplified from WT PRLR DNA, leading to one large band of a 240 bp. The A to G mutation introduces a second restriction site in PCR product amplified from alleles encoding this mutant, resulting in another band at 176 bp in heterozygous subjects.

Exon 6 PCR products (323 bp) were digested by XapI (ApoI) for 1 h at 37° C.; There is one restriction site in the PCR product amplified from WT PRLR DNA, leading to two bands of 142 &181 bp. This restriction site is abolished with A to C mutation, resulting in a band at 323 bp.

Figure 17:
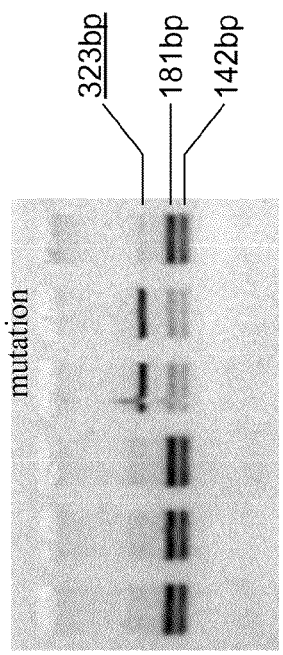
FIG. 17 shows the restriction profiles of PCR products obtained with WT PRLR and the mutants I76V and I146L. The bands specific of the mutants are underlined.
Figure 17:
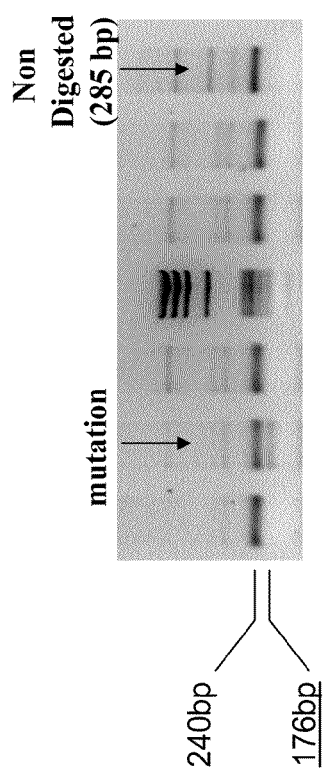

FIG. 17 shows the restriction profiles of PCR products obtained with WT PRLR and the mutants I76V and I146L. The bands specific of the mutants are underlined.

The invention claimed is:

1. A method for detecting whether a subject expresses a constitutively active mutant of the prolactin receptor (PRLR) comprising detecting a mutation in the PRLR gene in a nucleic acid sample previously obtained from said subject selected from:
   a mutation resulting in the expression of a constitutively active mutant prolactin receptor, wherein the Ile residue at position 146 is substituted by another amino acid residue selected from the group consisting of Leu, Met, Thr, Asn, Ser, Phe and Val; or
   a mutation resulting in the expression of a constitutively active mutant prolactin receptor wherein the Ile residue at position 76 is substituted by another amino acid residue selected from the group consisting of Leu, Met, Thr, Asn, Ser, Phe and Val
wherein the presence of the mutation indicates the presence of the constitutively active mutant.

2. The method of claim 1, wherein said mutation is:
   a mutation resulting in an Ile to Leu substitution at position 146;
   a mutation resulting in an Ile to Val substitution at position 76.

3. The method of claim 1, wherein the mutant PRLR comprises the amino acid sequence as set forth in SEQ ID NO: 1 with Val at position 76 and Leu at 146.

4. A method for evaluating whether a woman is prone to develop a breast disease selected from the group consisting of fibroadenoma, multiple fibroadenomas and hypermastia, the method comprising detecting a mutation in the PRLR gene in a nucleic acid sample previously obtained from said subject wherein the mutation is:
   a mutation resulting in the expression of a mutant prolactin receptor, wherein the Ile residue at position 146 is substituted by another amino acid residue selected from the group consisting of Leu, Met, Thr, Asn, Ser, Phe and Val; or
   a mutation resulting in the expression of a mutant prolactin receptor wherein the Ile residue at position 76 is substituted by another amino acid residue selected from the group consisting of Leu, Met, Thr, Asn, Ser, Phe and Val;
wherein the presence of the mutation indicates that the woman is prone to develop a breast disease selected from the group consisting of fibroadenoma, multiple fibroadenomas and hypermastia.

5. The method of claim 4, wherein the breast disease is multiple fibroadenomas.

6. A method for assessing the prognosis of a woman presenting with a breast disease selected from the group consisting of fibroadenoma, multiple fibroadenomas and hypermastia, comprising detecting a mutation in the PRLR gene in a nucleic acid sample previously obtained from said subject selected from:
   a mutation resulting in the expression of a mutant prolactin receptor, wherein the Ile residue at position 146 is substituted by another amino acid residue selected from the group consisting of Leu, Met, Thr, Asn, Ser, Phe and Val; or
   a mutation resulting in the expression of a mutant prolactin receptor wherein the Ile residue at position 76 is substituted by another amino acid residue selected from the group consisting of Leu, Met, Thr, Asn, Ser, Phe and Val
wherein the presence of the mutation indicates the prognosis of the woman.

7. The method of claim 6, wherein said breast disease is a fibroadenoma.

8. The method of claim 7, wherein the method evaluates the risk of the fibroadenoma evolving to multiple fibroadenomas.

9. The method of claim 6, wherein the mutant PRLR comprises the amino acid sequence as set forth in SEQ ID NO: 1 with Val at position 76 and Leu at 146.

* * * * *